US00PP31071P2

(12) United States Plant Patent
Olesen

(10) Patent No.: US PP31,071 P2
(45) Date of Patent: Nov. 19, 2019

(54) **MINIATURE *ROSA* PLANT NAMED 'POULPAR108'**

(50) Latin Name: ***Rosa* hybrid**
Varietal Denomination: Poulpar108

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,579

(22) Filed: Sep. 4, 2018

(51) Int. Cl.
*A01H 5/02* (2018.01)
*A01H 6/74* (2018.01)

(52) U.S. Cl.
USPC ..... Plt./122

(58) Field of Classification Search
USPC ..... Plt./101, 116, 119, 122
See application file for complete search history.

(56) References Cited

PUBLICATIONS

UPOV PLUTO: Plant Variety Database—cultivar denomination 'POULPAR108' (1 page) retrieved on May 7, 2019.*

* cited by examiner

*Primary Examiner* — Susan McCormick Ewoldt

(57) ABSTRACT

A new garden rose plant of the Miniature class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar108'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar108', originated as a single seedling from the stated cross.

The new variety may be distinguished from its male pollen parent and female seed parent primarily by the following characteristics. The male pollen parent plant has dark red flowers while the new variety has orange red flowers. The female seed parent plant has pink flowers while the new variety has orange red flowers.

The objective of the hybridization of this rose variety was to create a new and distinct variety with unique qualities, such as:

1. Uniform and abundant orange red flowers;
2. Vigorous, but compact growth when propagated on its own roots;
3. Exceptional disease resistance.

This combination of qualities is not present in previously available commercial cultivars of this type, known to the inventor, and distinguish 'Poulpar108' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar108' was selected in the spring of 2008 by the inventor as a single plant from the progeny of the aforementioned hybridization.

Asexual reproduction of 'Poulpar108' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpar108' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar108'.

Specifically illustrated in FIG. 1 of the drawings are flowers at various stages of development, receptacle with sepals detached showing reproductive flower parts, and petals detached.

Figure 1:
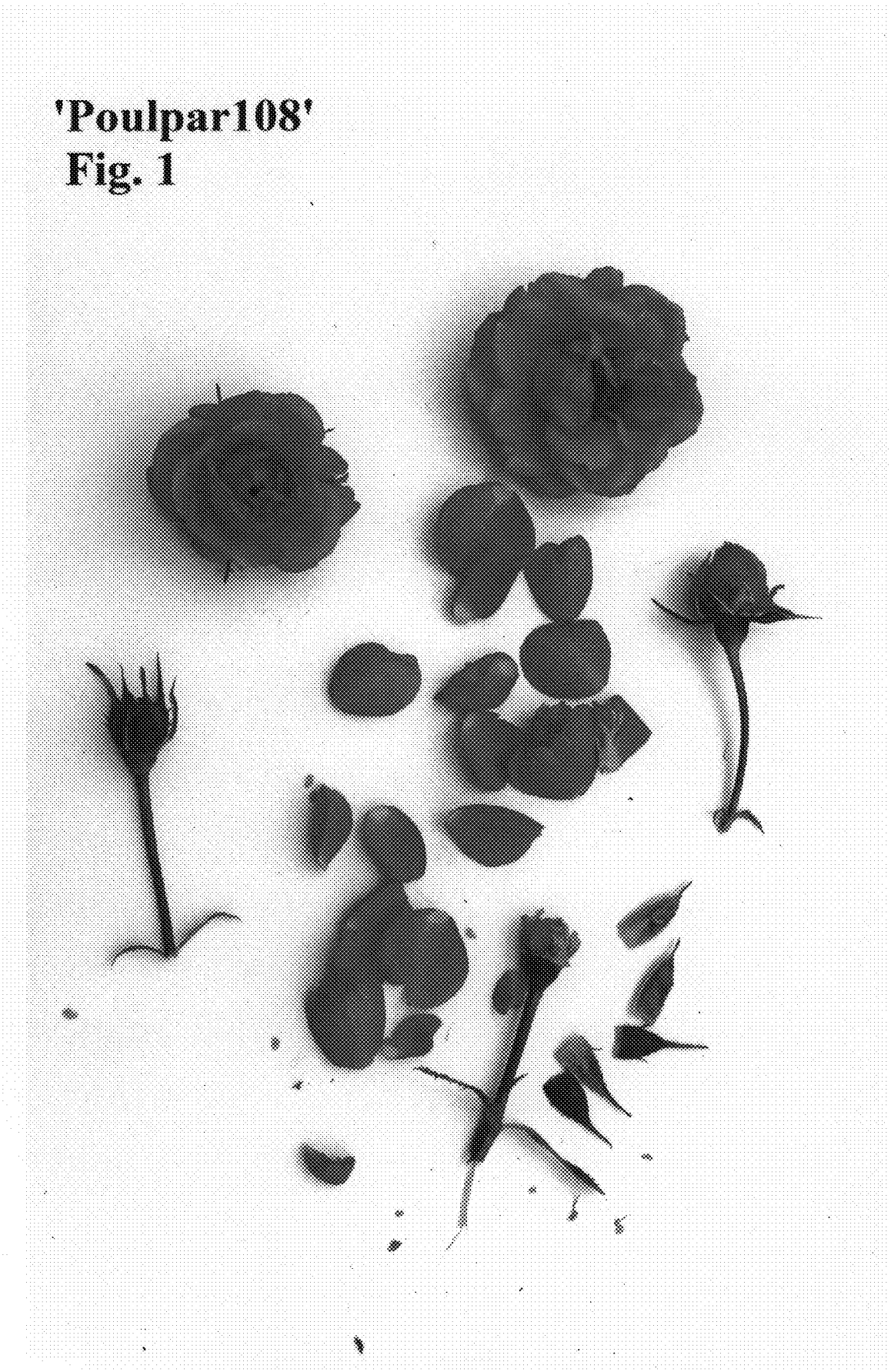
Figure 2:
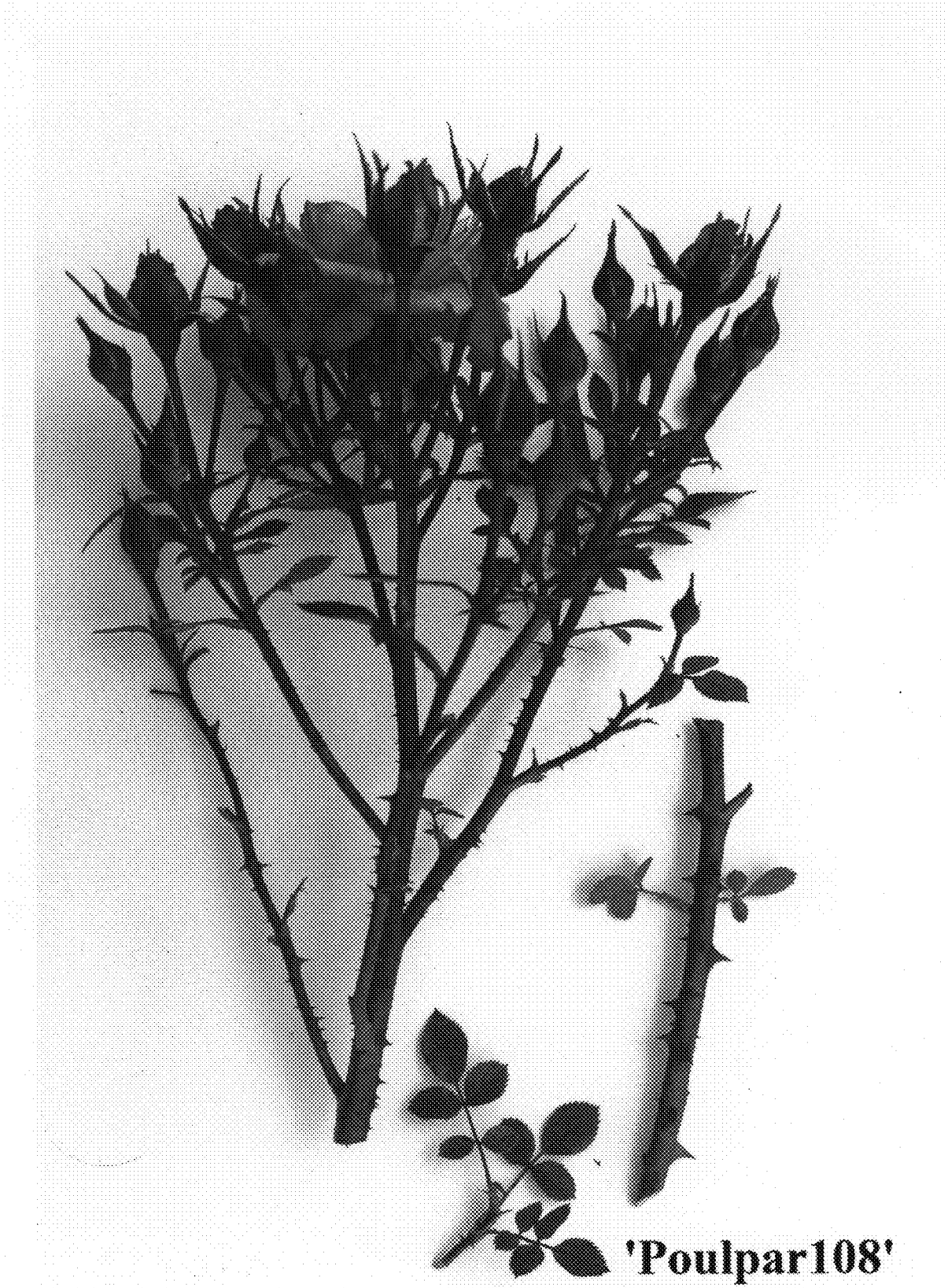

Specifically illustrated in FIG. 2 of the drawings is a cluster of flowers on a branch, showing peduncles and quantity of flowers on a branch, leaves, and bare stem exhibiting prickles. Plants shown are 2 years of age.

DETAILED DESCRIPTION OF THE VARIETY

The following is a description of 'Poulpar108', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar043', U.S. Plant Pat. No. 18,143 are compared to 'Poulpar108' in Chart 1.

CHART 1

| | 'Poulpar108' | 'Poulpar043' |
|---|---|---|
| Petal Count | 30 to 35 | 25 to 30 |
| Flower Diameter | 40 mm | 40 mm |
| General Tonality of Flower Color | Red Group 46D | Red Group 40A |

FLOWER AND FLOWER BUD

Blooming habit: Continuous.

Flower bud:

*Size*.—Upon opening, 20 mm in length from base of receptacle to end of bud. Bud diameter is 10 mm.

*Bud form*.—Urceolate.

*Bud color*.—As sepals divide petals are Red Group 46C.

*Sepal inner surface*.—Color: Yellow-Green Group 146B with intonations of Greyed-Purple Group 184B. Surface: Lightly pubescent.

*Sepal outer surface*.—Color: Yellow-Green Group 146A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—19 mm long, 6 mm wide.

*Receptacle*.—Texture: Smooth. Size: 5 mm in height, 8 mm wide. Color: Yellow-Green Group 144A with intonations of Greyed-Purple Group 184B. Shape: Campanulate.

*Pedicel*.—Surface: Smooth. Length: 30 mm. Diameter: 2 mm on average. Color: Yellow-Green Group 144A with intonations of Greyed-Purple Group 183A. Strength: Strong.

*Peduncle*.—Length: 2 to 10 cm. Diameter: About 3 mm. Color: Yellow-Green Group 144A with intonations of Greyed-Purple Group 183A. Texture: Rough with small prickles.

Flower bud development: Flower buds are borne singly or in cluster of five flower buds per stem.

Flower bloom:

*Fragrance*.—Strong perfume.

*Duration*.—The blooms have a duration on the plant of approximately 10 days. Petals fall cleanly away from plant after flowers have fully matured.

*Size*.—Flower diameter is 40 mm when open. Flower depth is 18 to 20 mm.

*Flower shape*.—High centered double, with a high pointed center which is tightly closed.

Petalage: Under normal conditions, flowers have about 30 to 35 petals.

General tonality of flower: Open flowers are Red Group 46D.

Petal color:

*Upon opening, outer petals*.—Upper surface: Red Group 41B. Lower surface: Red Group 43C.

*Upon opening, inner petals*.—Upper surface: Red Group 41B. Lower surface: Red Group 43C.

*Basal petal spots, upon opening*.—Upper surface: Yellow Group 10A. Lower surface: Yellow Group 4B.

*After opening, outer petals*.—Upper surface: Red Group 41B. Lower surface: Red Group 43C.

*After opening, inner petals*.—Upper surface: Red Group 41B. Lower surface: Red Group 43C.

*Basal petal spots, after opening*.—Upper surface: Yellow Group 10A. Lower surface: Yellow Group 4B.

Petals:

*Petal reflex*.—Somewhat reflexed.

*Margin*.—Entire and uniform. Moderate undulations.

*Shape*.—Broad and elliptic. Apex shape: Rounded. Base shape: Acute.

*Size*.—20 mm (l)×20 mm (w).

*Texture*.—Smooth.

*Thickness*.—Average.

Petaloids:

*Size*.—6 mm (l) by 4 mm (w).

*Quantity*.—About 3.

*Shape*.—Elliptical with an acute base and rounded apices.

*Color*.—Upper surface is Red Group 41B with a petaloid spot of Yellow Group 10A. Lower surface Red Group 43C with a petaloid spot of Yellow Group 4B.

Reproductive flower parts:

*Pollen*.—None observed.

*Anthers*.—Size: 2 mm in length. Color: Yellow Group 13B. Quantity: 50 on average.

*Filaments*.—Color: Yellow Group 5C, with intonations of Orange-Red Group N34C. Length: 3 mm.

*Pistils*.—Length: 4 mm. Quantity: 25 on average.

*Stigmas*.—Color: Greyed-Yellow Group 161D.

*Styles*.—Color: Greyed-Yellow Group 161D.

*Location of stigmas*.—Inferior in location relative to the length of the filaments and the height of the anthers.

*Hips*.—None Observed.

PLANT

Plant growth: Upright, somewhat bushy. Plants are about 35 cm in height, and 30 cm wide.

Stems:

*Color of juvenile growth*.—Yellow-Green Group 144A.

*Color of mature growth*.—Yellow-Green Group 146A with intonations of Greyed-Purple Group 183C.

*Length*.—Canes are about 17 cm from the base of the plant to the flowering portion.

*Diameter*.—About 6 mm.

*Internodes*.—On mature canes about 23 mm between nodes.

*Surface texture*.—Young wood: Rough with small prickles. Older wood: Rough with small prickles.

Long prickles:

*Incidence*.—10 prickles per 10 cm of stem.

*Size*.—Average length of prickles on mature stems is 5 mm.

*Shape*.—Upper portion is linear. Lower portion is concave.

*Color*.—Juvenile prickles: Greyed-Purple Group 184B. Mature prickles: Greyed-Purple Group 184B.

Plant foliage:

*Compound leaf.*—72 mm (l)×44 (w).

*Quantity.*—3 leaves per 10 cm of stem on average.

*Leaf bearing angle to the stem.*—45 degrees.

*Color of juvenile foliage.*—Upper side: Yellow-Green Group 147A with intonations of Greyed-Purple Group 183C. Lower side: Yellow-Green Group 148B with intonations of Greyed-Purple Group 183C

*Color of mature foliage.*—Upper side: Yellow-Green Group 147A. Lower side: Yellow-Green Group 147B.

Plant leaves and leaflets:

*Stipules.*—Size: 10 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 15 mm. Diameter: 2 mm. Upper surface color: Yellow-Green Group 144A with intonations of Greyed-Purple Group 183A. Lower surface color: Yellow-Green Group 144A.

*Rachis.*—Length: 23 mm. Upper surface color: Greyed-Purple Group 183A. Lower surface color: Yellow-Green Group 144A.

*Leaflet.*—Quantity: Normally 5 leaflets. Margins: Serrated. Size: Terminal leaflets are about 26 mm long, 17 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Miniature rose class named 'Poulpar108', substantially as illustrated and described herein, due to its abundant orange red flowers, disease resistance, and extended period of bloom.

* * * * *

'Poulpar108'

'Poulpar108'